(12) United States Patent
Schneider et al.

(10) Patent No.: US 9,857,327 B2
(45) Date of Patent: Jan. 2, 2018

(54) ELECTROCHEMICAL SENSOR

(71) Applicant: Mettler-Toledo AG, Greifensee (CH)

(72) Inventors: Ingo Schneider, Cham (CH); Fritz Baltensperger, Dietikon (CH); Corrado Barcella, Endingen (CH); Dario Meier, Baden (CH)

(73) Assignee: Mettler-Toledo GmbH, Greifensee (CH)

(*) Notice: Subject to any disclaimer, the term of this patent is extended or adjusted under 35 U.S.C. 154(b) by 185 days.

(21) Appl. No.: 14/709,537

(22) Filed: May 12, 2015

(65) Prior Publication Data
US 2015/0330940 A1    Nov. 19, 2015

(30) Foreign Application Priority Data

May 13, 2014    (EP) ..................... 14167998

(51) Int. Cl.
*G01N 27/414*    (2006.01)
*G01N 27/28*    (2006.01)

(52) U.S. Cl.
CPC ........... *G01N 27/414* (2013.01); *G01N 27/28* (2013.01)

(58) Field of Classification Search
CPC ............................. G01N 27/414; G01N 27/28
See application file for complete search history.

(56) References Cited

U.S. PATENT DOCUMENTS 5,902,467 A * 5/1999 Wang .................. H01M 2/1044
                                                    204/406
7,241,369 B2    7/2007 Van Hoorn
7,880,471 B2    2/2011 Fanselow et al.
8,877,026 B2   11/2014 Yamanouchi et al.
2014/0012098 A1  1/2014 Rieth

FOREIGN PATENT DOCUMENTS

DE    10 2009 001 632 A1    9/2010
DE    10 2009 026 991 A1    3/2011

OTHER PUBLICATIONS

Khanna, V.K. et al., Critical issues, processes and solutions in ISFET packaging, Microelectronics International, 2008, pp. 23-30, 25/2.
Oelssner, W. et al., Encapsulation of ISFET sensor chips, Sensors and Actuators B, 2005, pp. 104-117, 105.

* cited by examiner

*Primary Examiner* — J. Christopher Ball
(74) *Attorney, Agent, or Firm* — Standley Law Group LLP

(57) ABSTRACT

An electrochemical sensor, used with a measuring medium, has a sensor head (1), a sensor chip (6, 606) with a sensitive region (632), a sensor body (2) with an end piece (3, 503), a sealing means (10, 510, 610) and a pressing element (18, 618). The sensor body is connected to the sensor head. The end piece is hollow with a closed end region and a measuring opening (4, 504) that allows the measuring medium to contact the sensitive region, which is inside the end piece during operation. The sealing means surrounds the measuring opening, other than the sensitive region, and seals the inside of the end piece from the measuring medium during operation. The pressing element biases the sensor chip against the sealing means and the edge of the measuring opening. The end piece has an integral, gap-free design in the region that contacts the measuring medium during operation.

14 Claims, 3 Drawing Sheets

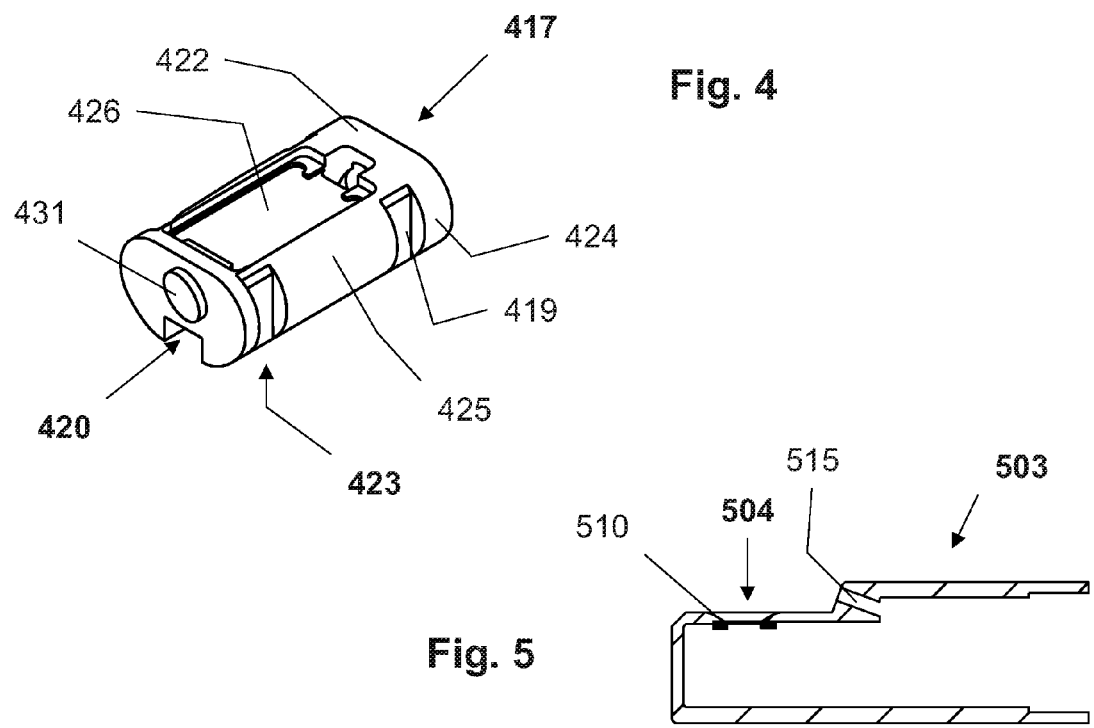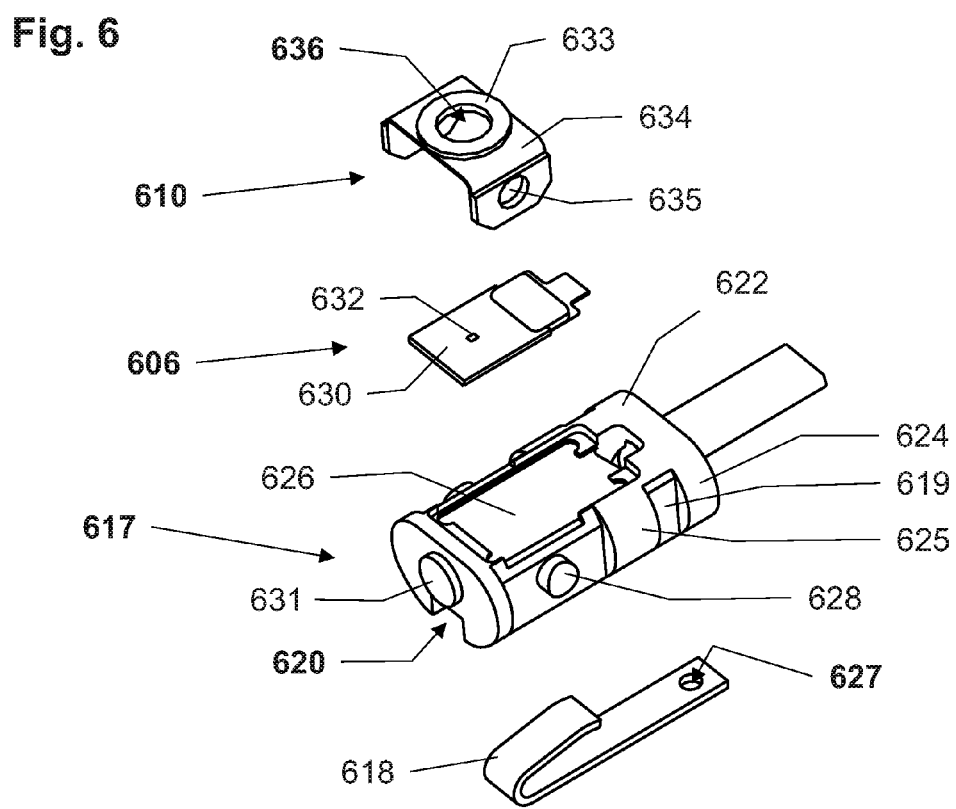

ELECTROCHEMICAL SENSOR

CROSS-REFERENCE TO RELATED APPLICATIONS

This application is entitled to benefit of a right of priority under 35 USC §119 from European patent application 14167998.5, filed on 13 May 2014, the content of which is incorporated by reference as if fully recited herein.

TECHNICAL FIELD

The disclosed invention relates to an electrochemical sensor with a sensor chip and the arrangement and installation thereof in the sensor.

BACKGROUND

Electrochemical sensors with a sensor chip are used in laboratories and also in production plants to detect different chemical and/or physical parameters. An example is a pH sensor with an ion-sensitive field effect transistor (ISFET) as sensor chip.

Use in production plants and under process conditions, in particular, requires the sensor to be extremely robust. A sensor chip such as an ISFET, for example, should, however, be in direct contact with the medium to be measured in order to take a measurement, which makes it necessary for the sensor to exhibit at least one opening. The sensor chip is arranged in the sensor in such a manner that at least the sensitive region thereof can be brought into contact with the measuring medium through this opening. Process-approved sensors frequently exhibit a substantially cylindrical sensor body with standard dimensions, so that these can easily be integrated into existing process plants.

A challenge is posed by the use of electrochemical sensors of this kind in biological, biotechnological, food-chemical and/or pharmaceutical process plants and also in laboratories in these sectors. Uses in these sectors require the sensor to be hygienic and satisfy the corresponding standards. A hygienic sensor is characterized in that wherever possible no substances are deposited on the sensor and/or are able to multiply there, as this kind of contamination causes biofouling, for example, and/or it can even contaminate an entire process.

It is therefore important in an application of this kind to ensure optimal encapsulation of the sensor chip in the sensor, which on the one hand allows direct contact between the sensitive region and the measuring medium and, on the other hand, at least guarantees a fluid-tight seal between the measuring medium and the inside of the sensor, so that no measuring medium is able to penetrate the sensor.

The possible ways of encapsulating sensor chips are described for example in W. Oelpner et al. "Encapsulation of ISFET Sensor Chips", Sensors and Actuators B 105 (2005) 104-117 and V. L. Khanna "Critical issues, processes and solutions in ISFET packaging", Microelectronics Int. 25/2 (2008) 23-30 and range from the simple adhesion of the sensor chip, through the use of an attachment with a sensor chip mounted between two seals (EP 1 396 718 A1) or the pouring of a hardenable filling substance into the inside of the sensor to pressing in with a stopper which presses the sensor chip against a seal enclosing the opening.

Known annular gasket s or also a laser-cut seal adapted to the sensor type can be used as seal, as for example disclosed in DE 10 2009 026 991 A1.

The disadvantage of the known sensors is that they frequently fail to meet the requirements made in fields such as for example biochemistry, biotechnology, food chemistry and/or pharmaceuticals, in relation to a hygienically configured sensor, as the sensor exhibits production-related cracks, gaps or undercuts in the region that comes into contact with the measuring medium and these allow the settlement and accumulation of substances from the measuring medium, as a result of which the service life of the sensor can be shortened due to the penetrating measuring medium and/or measuring errors can result, for example. The formation of gaps or cracks may be caused by the insertion of sealing elements in the sensor body, for example. These sealing elements are used to close off access to the sensor body, through which the sensor chip is introduced into the sensor body.

The object of the invention is therefore the development of an electrochemical sensor with a sensor chip which is in particular of hygienic design. In addition, the sensor should be easy to fit, in other words easily assembled.

SUMMARY

This object is solved by an electrochemical sensor for determining at least a physical and/or chemical parameter of a measuring medium. The sensor comprises a sensor head, a sensor chip with a sensitive region, a sensor body with an end piece, a sealing means and a pressing element. The sensor body is connected to the sensor head and the end piece is a hollow body with a closed end region and a measuring opening through which during operation a measuring medium is in contact with the sensitive region arranged inside the hollow body. During operation the sealing means surrounds the measuring opening omitting the sensitive region of the sensor chip and seals the inside of the end piece in respect of the measuring medium. The pressing element presses the sensor chip against the sealing means and the edge of the measuring opening. The sensor is characterized in that the hollow body of the end piece is of integral, gap-free design in the region in contact with the measuring medium during operation.

An electrochemical sensor configured in this way is particularly advantageous as the gap-free embodiment means that it can be used in the region in contact with the measuring medium in processes that make stringent requirements in terms of the hygienic design of the sensor too.

Further, the sensor comprises a chip carrier on which the sensor chip is arranged in the end piece. The use of a chip carrier simplifies the installation or introduction of the sensor chip into the end piece, as this can easily be introduced along with the chip carrier through a terminal, medium-averted opening in the end piece.

In its operating position, the end of the sensor containing the sensor chip is in contact with the measuring medium, in particular a sensitive region of the sensor chip. This end of the sensor is also referred to below as "medium-facing". Elements which are arranged on the side of the sensor facing away from the measuring medium are similarly referred to as "medium-averted".

The pressing element is preferably configured as a spring element and arranged between the chip carrier and a wall of the end piece, so that the spring force of said pressing element presses against the sensor chip and the sealing means at the edge of the measuring opening.

A spring element acting as the pressing element may press the chip carrier and therefore also the sensor chip using a defined force—the spring force of the spring element— against the measuring opening, in particular the edge thereof, and the sealing element surrounding the measuring opening. In this way, a medium-tight termination of the end piece can be achieved in the peripheral region of the measuring opening and, in addition, a suitable contact pressure of the sensor chip against the sealing means can be achieved by selecting a suitable spring element.

The sealing means may be an annular gasket, for example, which is arranged at least partially in a suitable groove in the end piece and/or in the sensor chip or sensor carrier. Likewise, a shaped seal may be used as the sealing means. In a further embodiment, the sealing means comprises a sealing ring and a mount. The sealing ring and mount may be produced integrally or in multiple pieces. The mount preferably comprises bent side parts, each having an opening which can engage with suitable projections on the chip carrier and thereby determine and/or fix the position of the sealing means on the chip carrier.

In a preferred exemplary embodiment, the end piece is made of a polymer material which at least meets current standards for hygienic requirements to be met by polymer materials used multiple times. PEEK (polyether ether ketone) is an example of a suitable polymer material.

The end piece may be advantageously produced integrally from the polymer material, so that said end piece can be produced in a gap-free and crack-free manner. In addition, the end piece may be of biocompatible design through the choice of a suitable polymer material and/or satisfy the US Pharmacopoeia's standard USP VI.

The chip carrier comprises a receiving means for the sensor chip and at least one projection as the fastening element for the sealing means. Furthermore, the chip carrier may comprise one or a plurality of external ribs and/or a projection.

The embodiment of the chip carrier is preferably adapted to the shape of the end piece, so that the chip carrier can simply be inserted in the end piece along with the sensor chip and/or the pressing element and positioned therein.

For this purpose, the end piece may comprise a terminal charging opening through which the sensor chip, the pressing element, the sealing means and/or the chip carrier are introduced into the end piece. These elements are configured in such a way that they can be introduced into the end piece without the need for tools where possible and positioned there.

In addition, the sealing means is arranged in the end piece in such a manner that during operation it seals the inside of the end piece, omitting the sensitive region of the sensor chip, in respect of the measuring medium.

Furthermore, the sensor may comprise a duct in the end piece as an electrolyte bridge or liquid junction through which during operation the measuring medium is in contact with an internal electrolyte.

Further, a diaphragm may be disposed in the duct which may be for example a pin or a pin-shaped element, for example, and which comprises a porous ceramic.

Furthermore, the sensor may comprise a reference electrode system with the internal electrolyte, a reference electrode and the electrolyte bridge or liquid junction.

A reference electrode system is in particular required when using a pH-sensitive sensor chip, since a stable reference value is needed in order to determine the pH value of the measuring medium. It is advantageous for the reference electrode to be arranged along with the pH-sensitive sensor chip in the sensor, as only one sensor then has to be introduced into the measuring medium in order to obtain a meaningful measurement.

The sensor chip preferably comprises a flexible circuit board on which an ISFET is arranged. A flexible circuit board or also a flex print is more flexible and can be more strongly deformed than other circuit boards, which is particularly advantageous for the installation of the sensor chip in the end piece.

In a further embodiment, the end piece may be filled with a filling material which fixes at least the sensor chip, the pressing element and/or the chip carrier in the end piece in the assembled state.

The filling material is preferably hardenable, as in the case of a polymer material, for example, which can easily be introduced into the end piece and hardened in situ there. The filling material is preferably a material that can be introduced into the end piece in liquid form and thereby fill the existing gaps between the components arranged in the end piece as completely as possible. Once the filling material has hardened, said components are fixed in their position and thereby contribute to a lasting and durable robustness of the sensor.

The end piece and the sensor body may be connected to one another via a first terminal coupling means configured in the end piece and a second terminal coupling means configured in the sensor body, wherein the first and second coupling means interact. The first and second coupling means may, for example, be configured as internal and external threads, as a kind of bayonet locking element and/or as elements latching with one another. The end piece may be fixedly connected to the sensor or, to be more precise, the shaft of the sensor body by means of the first and second coupling means. Likewise, the connection between the first and second coupling means may be a detachable connection, so that it is possible to replace the end piece. Depending on the total length of the sensor, the sensor body and the end piece may, in addition, be configured as a single component.

The gap-free and crack-free embodiment of the end piece requires the elements located inside the end piece to be introduced through an opening in the medium-averted end of the end piece.

This is in particular possible through the use of the chip carrier and the pressing element, which constitute a guide for the chip sensor and enable its highly precise placing and positioning in the end piece beneath the measuring opening. The pressing element preferably has a defined contact force with which the sensor chip is pressed from within against the periphery of the measuring opening and the sealing means surrounding the measuring opening.

The embodiment of the end piece and of the chip carrier particularly allows easy assembly of the end piece, so that this can be realized without the use of screws or clips. The chip carrier also prevents the sensor chip for from being too severely bent or too severely deformed in the short term for insertion.

BRIEF DESCRIPTION OF THE DRAWINGS

In the following, various exemplary embodiments of an electrochemical sensor according to the invention are described in greater detail with the help of the figures, wherein the same elements are provided with the same or similar reference numbers. In the figures:

FIG. 4 shows a three-dimensional view of a chip carrier;

FIG. 5 shows a sleeve of a further end piece with a sealing means in section; and FIG. 6 shows an arrangement of a further sealing means, a sensor chip, a further chip carrier and a pressing element as an exploded drawing.

DETAILED DESCRIPTION OF THE DRAWINGS

Figure 1:
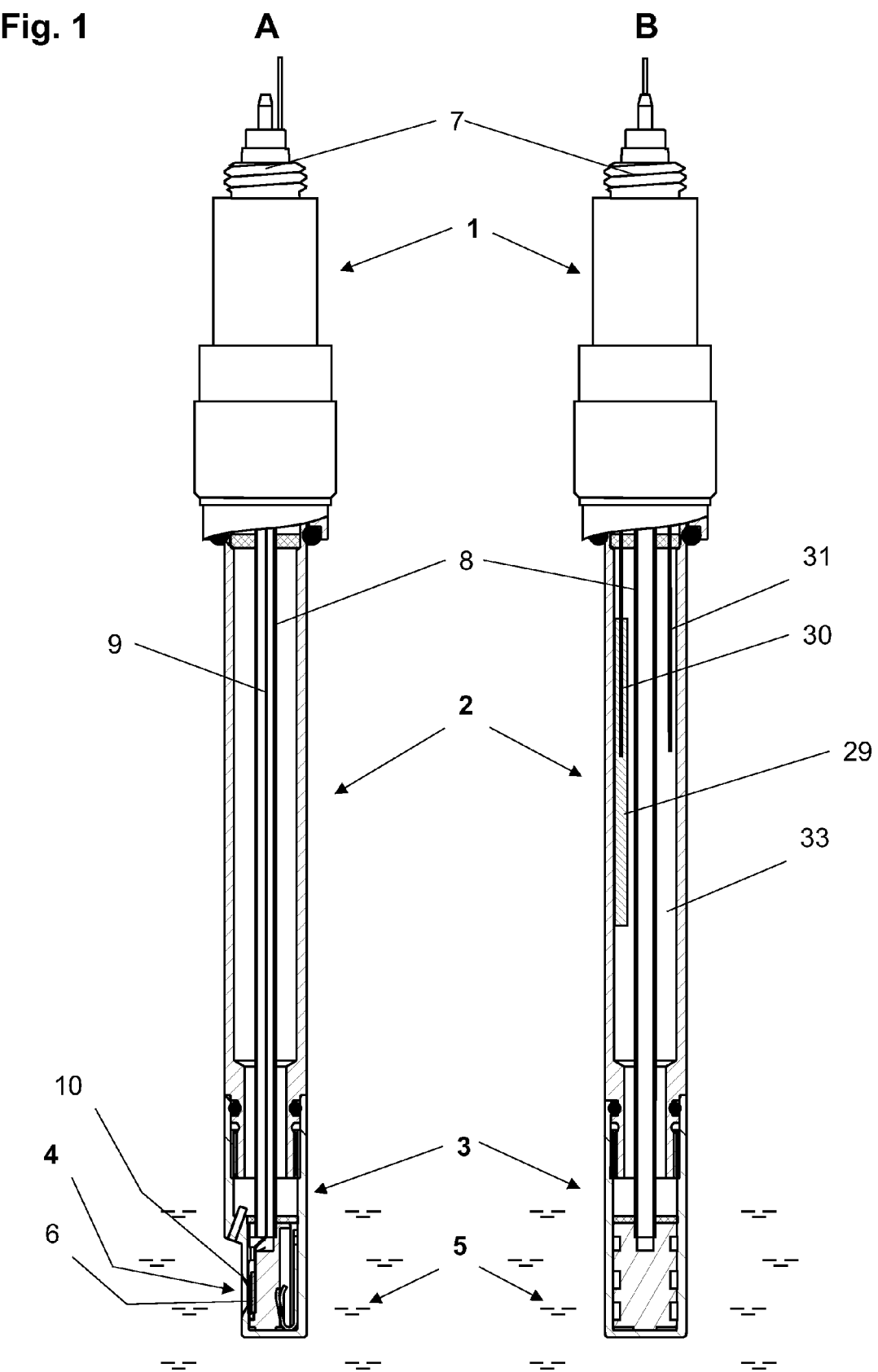
FIG. 1 shows two longitudinal sections A and B through an electrochemical sensor according to the invention along the centre longitudinal axis, wherein the two longitudinal sections are rotated about 90 degrees in respect of one another.

FIG. 1 shows two longitudinal sections A and B through an electrochemical sensor according to the invention, wherein parts of the sensor are closed and are not depicted in section. The two longitudinal sections A and B are rotated about 90 degrees in respect of one another and described together below. The sensor comprises a sensor head 1 and a sensor body 2 with an end piece 3 configured as a hollow body in which a measuring opening 4 is formed. The elements arranged in the end piece 3 are explained in greater detail with the help of FIGS. 2 and 3.

Located in the sensor head 1 are electronic connections and/or at least part of the sensor electronics which is required for control, recording the measuring results and/or transmitting the measuring results to a higher-level unit, for example a transmitter or a process control system. The sensor head 1 exhibits a standard commercial process connection 7. Electrochemical sensors with a plurality of sensor heads 1 and process connections 7 are known in the art and are not therefore described in detail here. The electrochemical sensor according to the invention may exhibit a sensor head 1, for example, which allows a wireless and/or inductive data and/or energy transmission, as well as a sensor head 1 which is connected via a suitable cable and/or a suitable plug connector with cable to the higher-level unit. Furthermore, at least part of the sensor electronics required to operate the sensor may be arranged in the sensor head 1.

The sensor body 2 is a substantially cylindrical or sleeve-shaped body, which length can vary depending on the area of application and the customer's wishes. The sensor body 2 may, for example, comprise a plastic, a polymer material, a metal, a metal alloy and/or mixtures thereof. In addition, an electrical cable 9 disposed in a cable conduit 8 can be identified in the sensor body 2, which cable establishes the connection between the electronics in the sensor head 1 and the sensor chip 6.

During operation, particularly during measurement, at least the end piece 3 of the sensor body 2 is immersed so far into a measuring medium 5 that the measuring opening 4 is in contact with the measuring medium 5, as indicated in FIG. 1. In a process plant, electrochemical sensors are frequently used along with a mounting part in which the sensor is inserted and which encloses a large part of the sensor—omitting the parts or elements that are in contact with the measuring medium during the measurement.

The measuring opening 4 constitutes an access to the inside of the end piece 3, more precisely to a sensor chip 6 which is arranged in the end piece in such a manner that a sensitive region of the sensor chip 6 is located in the measuring opening 4 and is in contact with the measuring medium during operation. The measuring opening 4 is sealed in respect of the sensor chip 6 and, above all, in respect of the inside of the end piece 3, omitting the sensitive region, using a suitable sealing means 10, so that the measuring medium 5 cannot penetrate the end piece 3 during operation.

The end piece 3 in particular is of gap-free design, at least in all regions coming into direct contact with the measuring medium 5 during operation. In addition, the surface of the end piece 3 is smoothly configured, at least in the contact region with the measuring medium, and all corners and edges of the end piece are rounded off. The end piece 3, like the sensor body 2, may for example comprise a plastic, polymer material, a metal, a metal alloy and/or mixtures thereof. The gap-free configuration, choice of material and smooth surfaces are particularly important when the sensor is used in sectors with stringent hygiene requirements, such as in biochemistry, biotechnology, food chemistry, biology or pharmaceuticals, as contamination through deposits of substances from the measuring medium and/or biofouling can thereby be prevented as far as possible.

Figure 2:
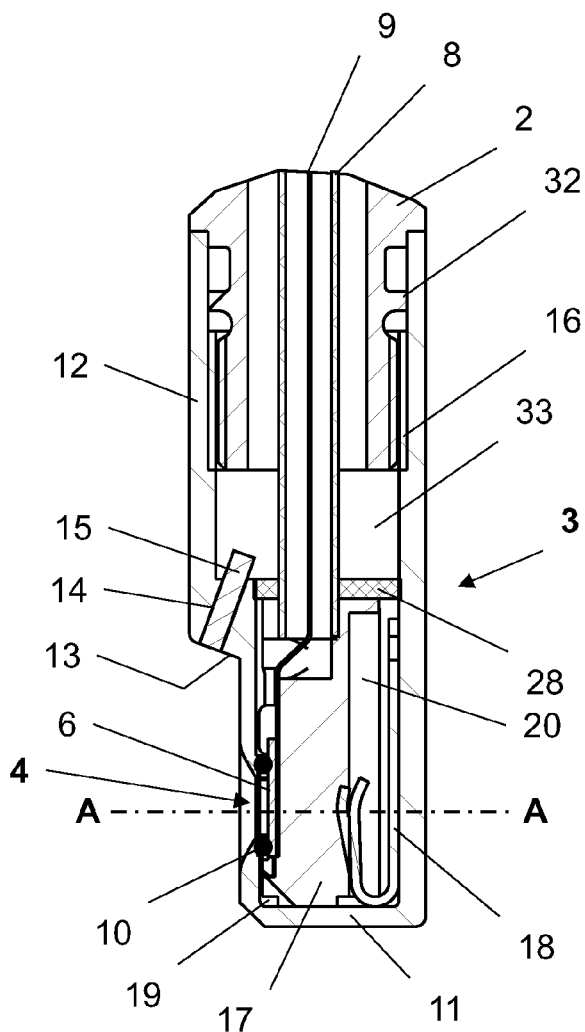
FIG. 2 shows an enlargement of the end piece of the sensor from FIG. 1 in section.

FIG. 2 shows the assembled end piece 3 in section in an enlargement of FIG. 1.

The end piece 3 is a substantially cylindrical hollow body, which medium-facing region 11 is designed to be terminally closed. The end piece also exhibits a flat region in which the measuring opening 4 is disposed. The liquid junction between the medium-facing region 11 and a medium-averted region 12 forms a shoulder 13 in which a duct 14 is configured, in which a diaphragm 15 of a reference electrode configured in the sensor is arranged during operation.

In addition to the diaphragm 15, the reference electrode comprises an internal electrolyte which is arranged in an electrolyte chamber 33 disposed in the inside of the sensor. During operation the internal electrolyte is in contact with the measuring medium 5 via the diaphragm 15 and in contact with the sensor head 1 via a conductor element 31. The internal electrolyte and the diaphragm 15, along with a reference electrode 29 configured as a cartridge and a further conductor element 30, create the reference electrode system of the sensor. A silver/silver chloride electrode, for example, may be used as the reference electrode 29. In a maintenance-free embodiment of the reference system, the internal electrolyte is preferably thickened, in other words mixed with a thickening agent. An aqueous, approx. 3 molar potassium chloride solution with the addition of a thickening agent such as glycerine, non-crosslinked polyacrylamide, starch derivatives or alginates, for example, may be used as the thickened internal electrolyte. The diaphragm 15 is used as the liquid junction of the reference electrode and may be made of a porous ceramic or porous PTFE (polytetrafluoroethylene), for example. Furthermore, bunches of platinum wire or open-junction or single-pore systems may also be used as liquid junction, the latter particularly along with a thickened internal electrolyte such as a hydrogel, for example.

A first coupling means 16 which serves to connect the end piece 3 to the medium-facing end of the sensor body 2 is configured in the medium-averted region 12. The sensor body 2 has a suitable second coupling means 32 for this purpose as a counterpart to the first coupling means 16. The first and second coupling means 16, 32 may, for example, be configured as an internal and external thread, as a kind of bayonet locking element and/or as elements latching with one another.

The measuring opening 4 which is configured on the end piece 3 on a face 21 formed by flattening, is sealed by a suitable sealing means 10 in respect of the inside of the end piece 3 and therefore the inside of the sensor, so that no measuring medium is able to penetrate the sensor during operation either.

The end piece 3 and also the sealing means 10 may be made of a polymer material. The end piece may be produced from a material which at least satisfies the current standards for hygienic requirements of polymer materials used multiple times. These materials include, among other things, natural PEEK. The end piece 3 may be directly formed from this material. A suitable fluorinated elastomer, for example Fluoroprene manufactured by Freudenberg, Germany, may be procured as the sealing means, which at least satisfies the current hygiene requirements of rubber and rubber-like materials which are used as product contact surfaces for dairy equipment.

The materials should preferably also be biocompatible and/or in conformity with USP VI. The sealing means 10 may be integrated in the end piece 3 and formed integrally therewith (see also FIG. 6). The sealing means 10 shown in FIGS. 1 to 3 may, for example, be an annular gasket made of a suitable polymer material.

Furthermore, the elements arranged in the assembled state in the end piece 3—a sensor chip 6, a chip carrier 17 and a pressing element 18—are shown in detail in FIG. 2.

The sensor chip 6 may, for example be a pH-sensitive ISFET on a flexible circuit board which is connected to the electronics in the sensor head via a cable 9. A flexible circuit board, for example a flex print, has the advantage that the circuit board has higher tolerances in relation to mechanical deformation than a traditional circuit board. The flexible circuit board comprises conductors for making contact with the ISFET which is fixedly connected or bonded to the circuit board. The gate region of the ISFET constitutes the sensitive region of the sensor chip 6 and is in direct contact with the measuring medium 5 through the measuring opening 4 during operation.

The sensor chip 6 is located on a chip carrier 17, the shape of which is substantially adapted to the medium-facing region 11 of the end piece 3 and substantially fills it. In the end piece 3, a sealing element 28 is disposed beneath the shoulder 13, which closes off the medium-facing region 11 of the end piece 3 and delimits the electrolyte chamber 33, so that the dividing element prevents the internal electrolyte penetrating the medium-facing region 11. The sealing element 28 may be a separate element, fixedly connected to the chip carrier 17 or configured as part of the chip carrier 17, in other words integrally produced therewith.

The chip carrier 17 exhibits faces aligned in parallel to one another which are connected by a centre part (see also FIGS. 4 and 5). The face turned towards the measuring opening 4 exhibits a recessed receiving means for the sensor chip 6 and is referred to in the following to distinguish it as the receiving face. The face opposite the receiving face is referred to in the following as the pressure face, as the pressing element 18 bears against the contact face in the assembled state.

The pressing element 18 substantially comprises a bent strip of a solid and yet flexible material, such as a metal or metal alloy, for example. A pressing element 18 configured in this way acts like a laminated spring and in the assembled state it presses the chip carrier 17 with the sensor chip with a defined spring force against the sealing means 10 and the periphery of the measuring opening 4. The pressing element 18 is of such a design that it exerts a uniform force—in this case a spring force—so that the sealing means 10 is substantially homogeneously compressed and the inside of the end piece 3 is thereby sealed in respect of the measuring medium. The use of a laminated spring offers the advantage of a particularly simple assembly of the sensor, which can take place by simply pushing the spring under the chip carrier. However, it is also conceivable for one or a plurality of (initially tensioned) coil springs to be used which are relaxed after the chip carrier has been fitted. The use of one or a plurality of elongated spring or screw elements which are tensioned inside the end piece between the chip carrier and the outer wall is also conceivable.

The pressing element 18 is, moreover, configured in such a manner that it can easily be inserted along with the chip carrier 17 and the sensor chip 6 through the open medium-averted end of the end piece 3 into the same and removed again. In this way, the assembly of the end piece 3 is particularly simple and, moreover, it is possible to test the functionality of a sensor chip 6 in the assembled state and replace it if necessary.

In addition, the inside space of the end piece 3 can still be filled with a hardenable filling material following assembly, which filling material fixes the elements disposed in the end piece in their positions after hardening and, in addition, exerts the contact force against the sealing means 10 or else the periphery of the measuring opening 4 independently of the force exerted by the pressing element 18. Through filling, the end piece 3 becomes particularly stable and robust, which is particularly favourable for the storage and handling of the end pieces, as a displacement of the elements in the inside of the end piece and/or an abatement of the spring tension of the pressing element can be prevented. If a filling material is used, it can be introduced following assembly into the gaps 19 formed in the chip carrier 17 and a recess 20 introduced, against which the pressing element 18 bears. The sealing element 28 then terminates the medium-facing region 11 of the end piece 3 filled with the filling material. The sealing element 28 may, for example, be placed on the already hardened filling material or the filling material may be introduced through the sealing element 28 into the medium-facing region 11 using a suitable implement, such as a syringe or a connection piece formed in the sealing element 28, and then hardened there. Epoxy-based compounds or also polyurethane-based or silicon-based compounds are particularly suitable as filling materials.

Figure 3:
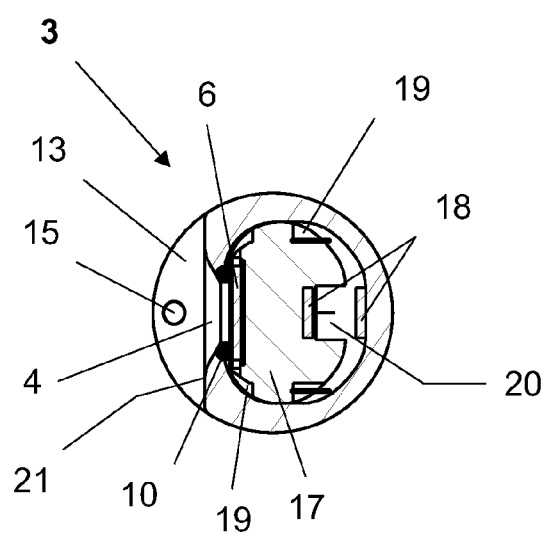
FIG. 3 shows a cross section through the end piece from FIG. 2 along plane A-A.

FIG. 3 shows a cross section through the end piece 3 shown in FIGS. 1 and 2 along plane A-A in the direction of the sensor head (see FIG. 2). The elements already referred to in connection with FIGS. 1 and 2 have the same reference numbers. The view in FIG. 3 shows both a face 21 in the flattened region in which the measuring opening 4 is arranged and also the shoulder 13, in which the duct with the diaphragm 15 can be identified.

The chip carrier 17 on which the sensor chip 6 is arranged is pressed by the pressing element 18 against the sealing means 10 and the periphery of the measuring opening 4. The gaps 19 that have not already been filled by the chip carrier 17 inside the end piece 3 or, to be more precise, the medium-facing region, and also the recess 20 for the pressing element can be filled with a filling material which fixes the elements in the end piece 3 after hardening and makes the contact force of the chip carrier 17 and the sensor chip 6 in respect of the sealing means 10 independent of the contact force of the pressing element 18.

FIG. 4 shows in a perspective representation an embodiment of the chip carrier 417 which can be used in an electrochemical sensor according to the invention. The chip carrier 417 exhibits two faces 422, 423 aligned parallel to one another which are connected by a centre part 425 provided with external ribs 424. The face 422 exhibits a recessed receiving means 426 for the sensor chip and is referred to in the following to distinguish it as the receiving face 422. The face 423 lying opposite the receiving face 422 is referred to below as the contact face 423. A recess 420 is located in the contact face 423 for receiving part of the pressing element, so that in the installed state in the recess 420 the pressing element bears against the contact face 423. In addition, the chip carrier 417 has a substantially circular stamped projection 431 in this case which strikes the medium-facing end of the end piece in the installed state, creating at least one fillable gap. The gaps in the end piece not filled by the chip carrier 417 can be filled with a filling material which fixes the elements disposed in the end piece in their positions when it has hardened. The embodiment of the chip carrier 417 with external ribs 424 and projection 431 therefore serves firstly to position the chip carrier 417 in the end piece, as they are in contact with the outer sleeve of the end piece, in addition the hardenable filling material can be introduced into the gaps 419 or channels formed between the external ribs 424 and also the recess 420 and hardened there. The chip carrier 417 shown in FIG. 4 may, for example, be used with the sealing means described in connection with FIGS. 1 to 3.

FIG. 5 shows a further embodiment of an end piece 503 with a duct 515 for a diaphragm and a measuring opening 504 in cross section, wherein in this embodiment a sealing means 510 is already arranged on an internal wall of the end piece 503 in such a manner that it surrounds the measuring opening 504. The sealing means 510 is preferably arranged in a suitable groove or flute in the internal wall of the end piece 503. Likewise, the sealing means 510 may be fastened to the internal wall of the end piece 503.

A further embodiment of a chip carrier 617 and of a sealing means 610 along with a sensor chip 606 and a pressing element 618 are shown in FIG. 6 in the form of an exploded representation.

The pressing element 618 is substantially a laminated spring made of one of the previously described materials. As can be identified here, the pressing element 618 exhibits a bore or opening 627 at the medium-averted end, which surrounds a knob formed on the chip carrier 617 in the assembled state, which knob cannot be seen in this view, as a result of which the pressing element 618 adopts a defined position in relation to the chip carrier 617.

The chip carrier 617 shown in FIG. 6 largely corresponds to the chip carrier 417 described in FIG. 4. Similar components are labelled using similar reference numbers and reference is made to the description of FIG. 4 for a detailed description of these elements. Unlike FIG. 4, the chip carrier 617 exhibits projections 628 on both sides of the centre part 625 which interact with counterparts on the sealing means 610 and serve to bear against or fasten the sealing means 610 following insertion of the sensor chip 606 on the chip carrier 617. In this way, the positions of the chip carrier 617, the sensor chip 606 and the sealing means 610 in respect of one another can be fixed.

The sensor chip 606 comprises a sensitive element 632 with a sensitive region which is mounted on a substrate and/or a carrier 630. The sensitive element 632 may be a pH-sensitive ISFET, for example, which is arranged on a flexible circuit board as the carrier 630. A flexible circuit board is also known as a flex print and has the advantage that the circuit board allows higher tolerances in respect of mechanical deformation than a traditional circuit board. The flexible circuit board comprises conductors for establishing contact with the ISFET which is fixedly connected or bonded to the circuit board. The gate region of the ISFET represents the sensitive region of the sensor chip 606 and is in direct contact with the measuring medium through the measuring opening during operation. The sensor chip 606 is inserted in the recess 626 of the chip carrier 617 and can in addition be fixed in the recess 626 by adhesion, for example.

Furthermore, a further embodiment of the sealing means 610 is shown in FIG. 6 which comprises a sealing ring 633 on a mount 634 with two lateral openings 635 and a further opening 636 which is delimited by the sealing ring 633 and which is used to establish contact between the sensitive region and the measuring medium.

The sealing means 610 is preferably integrally configured, which is possible particularly when using suitable polymer materials. The sealing means 610 is configured as a substantially flat plate and then changed into the shape shown by bending the outer parts of the plate. Likewise, it is possible to configure the mount 634 with the openings 635 separately and fasten a suitable sealing ring 633 to said mount 634, wherein the mount 634 is provided and/or configured with a suitable opening, about which the sealing ring 633 is arranged. Suitable materials are, for example, EPDM (ethylene propylene diene monomer), fluoroprene or NBR (nitrile butadiene rubber), wherein the sealing ring 633 in particular should comply with the current hygiene requirements relating to rubber and rubber-like materials which are used as product-contact surfaces for dairy equipment.

The two openings 635 in the bent-down side parts of the mount 634 represent counterparts for the projections 628 on the chip carrier and allow the sealing means 610 to be fastened to the chip carrier 617 via the sensor chip 606. In this way, a compact component is produced in which the position of the sealing ring 636 is prescribed in relation to the sensitive region of the sensitive element 632, which greatly simplifies the installation of these elements in an end piece of a sensor according to the invention.

Although the invention has been described by depicting specific exemplary embodiments, it is evident that numerous further embodiments can be created in the knowledge of the present invention, for example by combining the features of the individual exemplary embodiments with one another and/or replacing individual functional units of the exemplary embodiments. In particular, alongside the sealing means shown, O-rings or shaped seals known in the art can also be used, which are mounted in a groove in the end piece and/or in the mount shown in FIG. 6, for example. Furthermore, rather than pH-sensitive ISFETs, other ISFETs or even other sensitive elements can be used which are preferably likewise in contact with the measuring medium via a sensitive region during operation. The shape of the chip carrier can be adapted to the end piece to be used and/or the sensor chip, wherein recesses are to be realized for a filling material, in the event that the elements are to be fixed in the end piece using a hardenable filling material.

What is claimed is:

1. A sensor for electrochemically determining, for a measuring medium, at least one of: a physical and a chemical parameter, the sensor comprising:
   a sensor head;
   a sensor chip, having a sensitive region;
   a sensor body, connected to the sensor head and comprising:
      a chip carrier on which the sensor chip is arranged during operation;
      an end piece that is a hollow body with a closed end region and a measuring opening through which the measuring medium is in contact with the sensitive region, the end piece having an integral, gap-free design in the region in contact with the measuring medium during operation;
a means for sealing that surrounds the measuring opening, omitting the sensitive region, and that, during operation, seals the inside of the end piece in respect of the measuring medium; and
a pressing element that biases the sensor chip against the sealing means and an edge of the measuring opening.

2. The sensor of claim 1, wherein:
the chip carrier comprises at least one of: a means for receiving the sensor chip and a fastening element for the sealing means.

3. The sensor of claim 1, wherein:
the end piece comprises a terminal charging opening, through which at least one of: the sensor chip, the pressing element, the sealing means and the chip carrier are introduced into the end piece.

4. The sensor of claim 1, wherein:
the pressing element comprises a spring element, arranged between the chip carrier and a wall of the end piece, a spring force provided thereby pressing against the chip carrier with the sensor chip and the sealing means against an edge of the measuring opening.

5. The sensor of claim 1, wherein:
the sealing means is a shaped seal comprising a sealing ring arranged on a mount.

6. The sensor of claim 1, wherein:
the end piece is made of a polymer material.

7. The sensor of claim 1, wherein:
the end piece contains a duct as liquid junction through which the measuring medium is in contact with an internal electrolyte during operation.

8. The sensor of claim 7, further comprising:
a diaphragm, arranged in the duct as the liquid junction.

9. The sensor of claim 1, further comprising:
a reference electrode system with the internal electrolyte, a reference electrode and the liquid junction.

10. The sensor of claim 1, wherein:
the sensor chip is arranged with an ion-sensitive field effect transistor (ISFET) on a flexible circuit board.

11. The sensor of claim 1, further comprising:
a filling material that fills the end piece, securing in an assembled state at least one of the sensor chip, the pressing element and the chip carrier therein.

12. The sensor of claim 1, further comprising:
a first terminal coupling means, which is a part of the end piece; and
a second terminal coupling means, which is part of the sensor body, such that the respective terminal coupling means interact to connect the end piece to the sensor body.

13. The sensor of claim 2, wherein:
the end piece contains a duct as liquid junction through which the measuring medium is in contact with an internal electrolyte during operation.

14. The sensor of claim 13, further comprising:
a diaphragm, arranged in the duct as the liquid junction.

* * * * *